(12) United States Patent
Kleiman

(10) Patent No.: US 6,668,184 B1
(45) Date of Patent: Dec. 23, 2003

(54) SYSTEM FOR AND METHOD OF SYNCHRONIZING AN IMAGE DATA RECEIVER AND AN MR IMAGING ACQUISITION SLICE

(75) Inventor: Felix Kleiman, Haifa (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 135 days.

(21) Appl. No.: 09/740,592

(22) Filed: Dec. 19, 2000

(51) Int. Cl.[7] ................................................ A61B 5/05
(52) U.S. Cl. ...................................................... 600/422
(58) Field of Search ................................ 600/422, 421, 600/425, 407, 410

(56) References Cited

U.S. PATENT DOCUMENTS

| | | | | |
|---|---|---|---|---|
| 4,812,753 A | * | 3/1989 | Fuderer et al. .............. 324/307 |
| 5,211,165 A | | 5/1993 | Dumoulin et al. ........ 128/653.1 |
| 5,216,367 A | * | 6/1993 | Mori .......................... 324/318 |
| 5,318,025 A | | 6/1994 | Dumoulin et al. ........ 128/653.2 |
| 5,353,795 A | | 10/1994 | Souza et al. .............. 128/653.2 |
| 5,377,678 A | | 1/1995 | Dumoulin et al. ........ 128/653.1 |
| 5,377,679 A | * | 1/1995 | Machida et al. ............. 600/422 |
| 5,394,087 A | * | 2/1995 | Molyneaux .................. 324/318 |
| 5,416,413 A | * | 5/1995 | Leussler ...................... 324/318 |
| 5,715,822 A | | 2/1998 | Watkins et al. ........... 128/653.5 |
| 5,722,410 A | * | 3/1998 | NessAiver ................... 600/422 |
| 5,743,264 A | * | 4/1998 | Bonutti ....................... 600/415 |
| 5,898,306 A | | 4/1999 | Liu et al. ..................... 324/322 |
| 5,914,600 A | | 6/1999 | Pulyer ......................... 324/319 |
| 5,917,324 A | | 6/1999 | Leussler ...................... 324/318 |
| 5,933,007 A | | 8/1999 | Schommer et al. ......... 324/318 |
| 5,947,900 A | | 9/1999 | Derbyshire et al. ......... 600/410 |
| 5,999,000 A | | 12/1999 | Srinivasan .................. 324/318 |
| 6,157,193 A | * | 12/2000 | Renz et al. .................. 324/318 |
| 6,275,721 B1 | * | 8/2001 | Darrow et al. .............. 600/410 |
| 6,289,233 B1 | * | 9/2001 | Dumoulin et al. .......... 600/410 |
| 6,430,428 B1 | * | 8/2002 | Lindstedt .................... 600/410 |

OTHER PUBLICATIONS

U.S. patent application Ser. No. 09/729,601, Kleiman et al., filed Dec. 4, 2000.

* cited by examiner

*Primary Examiner*—Daniel Robinson
(74) *Attorney, Agent, or Firm*—Foley & Lardner; Carl B. Horton

(57) ABSTRACT

A magnetic resonance (MR) imaging system having an apparatus and method for providing appropriately located MR images acquired using a surface coil is disclosed herein. The system includes a controller configured to automatically synchronize a position of an image acquisition plane with respect to a position of the surface coil. To perform the synchronization, the system further includes a monitoring apparatus to monitor at least one of the position of the image acquisition plane and the surface coil.

22 Claims, 2 Drawing Sheets

SYSTEM FOR AND METHOD OF SYNCHRONIZING AN IMAGE DATA RECEIVER AND AN MR IMAGING ACQUISITION SLICE

BACKGROUND OF THE INVENTION

The present invention relates generally to imaging systems. More particularly, the present invention relates to an imaging system configured to track an image data receiver included therein to generate improved images.

When an object of interest, such as human tissue, is subjected to a uniform magnetic field (polarizing field Bo, along the z-direction in a Cartesian coordinate system denoted as x, y, and z), the individual magnetic moments of the spins in the tissue attempt to align with this polarizing field, but precess about it at their characteristic Larmor frequency. If such an object of interest, or tissue, is further subjected to a magnetic field (excitation field $B_1$) which is in the x-y plane and which is near the Larmor frequency, the net aligned moment ($M_z$,) may be rotated or "tipped" at a certain tipping angle into the x-y plane to produce a net transverse magnetic moment ($M_t$). Upon termination of excitation field $B_1$, signals are emitted by the excited spins.

In order to utilize these signals to produce a magnetic resonance (MR) image, the object of interest is also subjected to linear magnetic field gradients ($G_x$, $G_y$, and $G_z$). Typically, the object to be imaged is scanned by a sequence of measurement cycles in which these gradient waveforms vary according to the particular localization method being used. The linear gradients are configured to encode the emitted signals with spatial information such that the resulting set of received MR signals may be processed and reconstructed as a MR image.

When imaging anatomy located near the surface of a patient's body, a surface radio frequency (RF) coil, which is fairly small in size, may be used to produce high quality MR images. Since the signal-to-noise ratio (SNR) is higher for smaller RF coils than for larger RF coils, such as, body RF coils, when only a small region of the patient's body needs to be imaged, smaller RF coils can be used to produce the highest quality images. However, very small surface coils have a disadvantage in that they are difficult to position properly relative to the anatomy of interest. To facilitate repositioning of the surface coil, MR imaging systems are configured to permit an operator to have access to and interact with the patient positioned therein (generally referred to as open MR imaging systems). Accordingly, during a given procedure, the operator has the freedom to move in the vicinity of the patient and adjust the position of the surface coil relative to the patient's body, as needed, without disturbing the patient's position relative to the MR imaging system (i.e., without removing the patient from the magnet(s) of the MR imaging system).

Moreover, images acquired using a small surface coil correspondingly have a small field of view. Thus, when the operator is presented with such a small field of view image, it is very difficult for the operator to accurately identify the part of the anatomy being displayed. This would be analogous to the operator viewing a previously unseen room under low lighting conditions using only a narrow beam flashlight. He/she would have difficulty identifying where he/she is in the room and what he/she is looking at.

Still another shortcoming associated with surface coils is that when the surface coil is moved to a new location on the patient's body, it is difficult to correctly position the surface coil relative to the acquisition slice. The surface coil should receive emitted MR signals from at least a prescribed acquisition slice to provide an image of the acquisition slice and not another region of the patient's body. In other words, the images acquired should display anatomy located at the acquisition slice and such anatomy should be displayed at approximately the center of the images.

Thus, there is a need for a system and method that permits one or more movements or positioning of the surface coil relative to the patient during a given procedure without generating MR images with incorrect image locations. There is a further need for a system and method that overcomes the difficulty in anatomy identification due to small field of view images resulting from the use of surface coils.

BRIEF SUMMARY OF THE INVENTION

One embodiment of the invention relates to a magnetic resonance (MR) imaging system including a surface coil configured to generate an MR image having an appropriate image location. The system includes a controller configured to automatically synchronize a position of an image acquisition plane with respect to a position of the surface coil. Each of the position of the image acquisition plane and the surface coil is defined by at least a location and an orientation.

Another embodiment of the invention relates to a method of generating a magnetic resonance (MR) image having an appropriate image location in an MR imaging system including a surface coil. The method includes monitoring a position of at least one of an image acquisition plane and the surface coil. The method further includes coordinating the position of the image acquisition plane with respect to the position of the surface coil. Each of the position of the image acquisition plane and the surface coil is defined by at least a location and an orientation.

Still another embodiment of the invention relates to a system for generating a magnetic resonance (MR) image having an appropriate image location in an MR imaging system including a surface coil. The system includes means for monitoring a position of at least one of an image acquisition plane and the surface coil. The system further includes means for coordinating the position of the image acquisition plane with respect to the position of the surface coil. Each of the position of the image acquisition plane and the surface coil is defined by at least a location and an orientation.

BRIEF DESCRIPTION OF THE DRAWINGS

The preferred embodiment will become more fully understood from the following detailed description, taken in conjunction with the accompanying drawings, wherein like reference numerals denote like elements, in which.

DETAILED DESCRIPTION OF THE EXEMPLARY EMBODIMENTS

Figure 1:
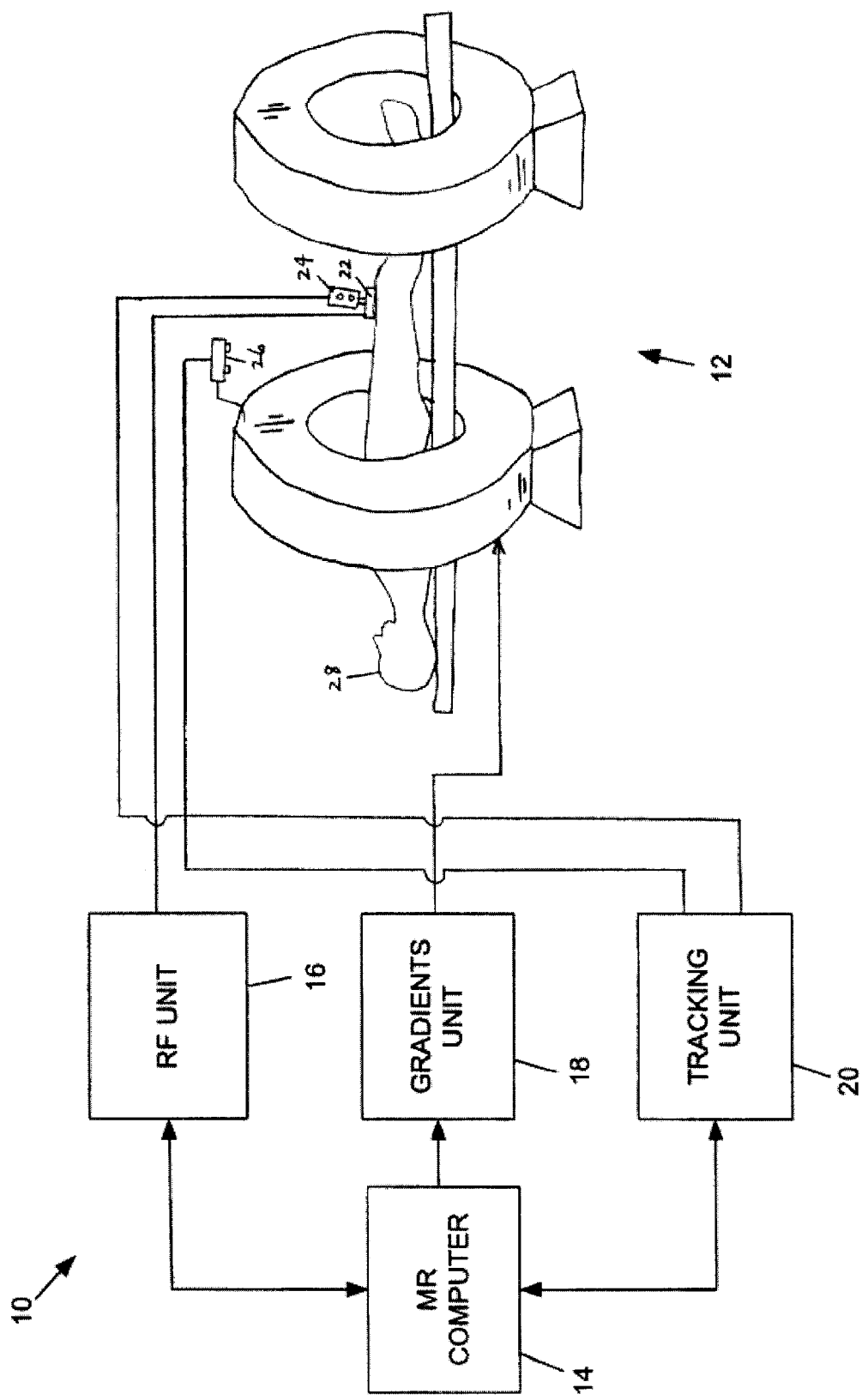
FIG. 1 is a block diagram of a magnetic resonance (MR) imaging system which employs an embodiment of the present invention.

Referring to FIG. 1, there are shown the major components of a magnetic resonance (MR) imaging system 10. System 10 includes an open magnet unit 12, an MR computer 14, a radio frequency (RF) unit 16, a gradients unit 18, a tracking unit 20, a surface RF coil 22, a tracking handpiece 24, and a locator 26. System 10 is configured to track the position and orientation of surface coil 22 as it is moved around on the surface of a patient 28 and to utilize this tracked position and orientation to prescribe an acquisition imaging plane to be acquired in real-time.

Patient 28 is preferably placed in open magnet unit 12 with a region of interest of patient 28 being positioned at or near the isocenter defined by one or more magnets of open magnet unit 12. Open magnet unit 12 is configured to permit an operator (e.g., a physician) to have access to patient 28, and in particular, the region of interest of patient 28, during a given scan. As such, the operator can move or reposition patient 28 relative to open magnet unit 12 and/or move or reposition surface coil 22 relative to patient 28.

For example, open magnet unit 12 shown in FIG. 1 comprises a pair of magnet rings along a common longitudinal axis with a gap therebetween. Alternatively, open magnet unit 12 may comprise a pair of parallel vertical plate magnets with a gap therebetween, a pair of parallel horizontal plate magnets with a gap therebetween, or a whole body coil (e.g., a cylindrical magnet) that is 1 to 1.5 meters in length.

Each of RF unit 16, gradients unit 18, and tracking unit 20 couples to MR computer 14. In turn, RF unit 16 couples to surface coil 22, and gradients unit 18 couples to open magnet unit 12. Tracking unit 20 couples to each of tracking handpiece 24 and locator 26. Tracking handpiece 24 couples to surface coil 22. Locator 26 mounts to open magnet unit 12, the ceiling, or other locations where it will be in proximity to tracking handpiece 24, such that locator 26 and tracking handpiece 24 will be in communication with each other. Tracking unit 20, tracking handpiece 24, and locator 26 comprise a tracking system of system 10.

MR computer 14 is configured to provide scan sequence commands to open magnet unit 12, via RF unit 16 and gradients unit 18, to obtain MR images of the region of interest of patient 28 (i.e., performs the imaging function). RF unit 16 and gradients unit 18 receive data regarding the timing, strength, and shape of the RF and gradient pulses, respectively, to be produced during a given scan from MR computer 14. In turn, RF unit 16 and gradients unit 18 apply such pulse or waveform data to appropriate RF and gradient coils in system 10 to produce the prescribed RF and gradient waveforms. The resulting MR signals radiated by the excited nuclei in the region of interest of patient 28 can then be picked up by surface coil 22 for reconstruction into one or more MR images in MR computer 14.

To perform this imaging function, MR computer 14 (also referred to as a controller) includes a processor, a memory, input/output devices, digital or analog circuitry, and/or pulse generation apparatus. RF unit 16 includes a RF amplifier, an RF preamplifier, and a transmit/receive switch, and gradients unit 18 includes gradient amplifiers.

MR computer 14 also interfaces with tracking unit 20 to synchronize the position (e.g., the location and orientation) of an image acquisition plane or slice with the position (e.g., the location and orientation) of surface coil 22 tracked by the tracking system.

In FIG. 1, surface coil 22 is configured to be a transmitter and receiver coil such as is well known in the art. Surface coil 22 is approximately 2–15 centimeters in width. Alternatively, surface coil 22 may be just a receiver with the transmitter capabilities being provided by other components in system 10. Because surface coil 22 is relatively small, its ability to receive or pick-up MR signals emitted from excited tissue is also fairly limited. Thus, in order to obtain MR images that the operator can identify and which are of high signal-to-noise ratio, it is preferable to prescribe the pulses and waveforms, in particular, the gradient waveforms, such that the position of the acquisition slice defined therefrom will track the position of surface coil 22.

Figure 2:
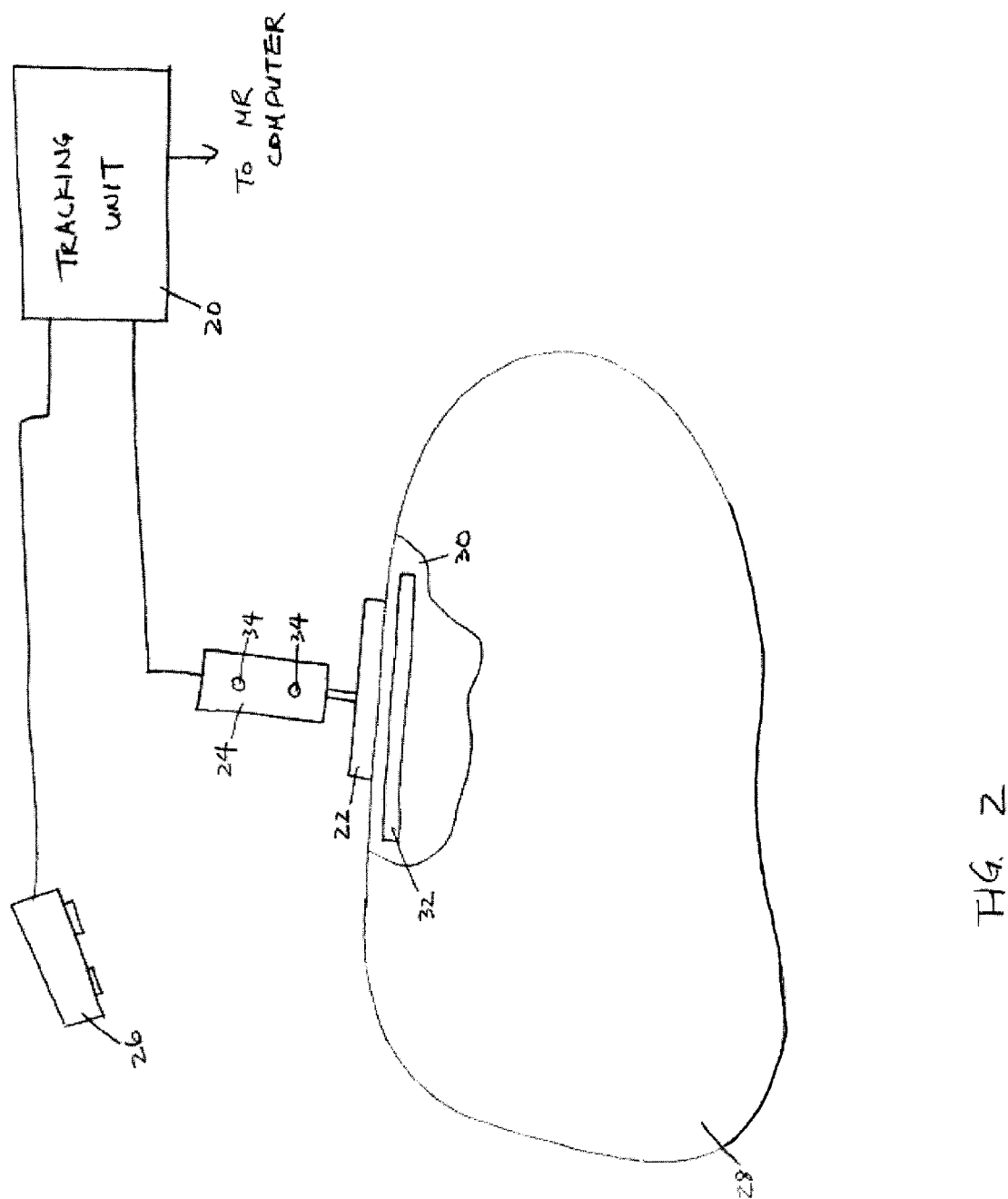
FIG. 2 is a block diagram of a tracking system which forms a part of the MR imaging system of FIG. 1.

Preferably, a region of interest 30 of patient 28 is identified prior to a scan (see FIG. 2). Next, surface coil 22 is positioned on patient 28 proximate to region of interest 30 (e.g., surface coil 22 is positioned above region of interest 30). In this embodiment, surface coil 22 functions as a pointer or indicator of the operator's desired region of interest to be imaged. Tracking handpiece 24, which is coupled to surface coil 22, is in continuous or periodic communication with locator 26 such that the position of tracking handpiece 24 (and hence, surface coil 22) can be tracked or monitored relative to a reference point, a point on patient 28, or in absolute coordinates in real-time or quasi real-time. Tracking unit 20 processes data from tracking handpiece 24 and locator 26 to generate tracking data associated with the position of surface coil 22.

MR computer 14 uses this tracking data to prescribe the position of an acquisition slice 32 such that the anatomy shown in each MR image is the anatomy that surface coil 22 is optimally positioned to pick-up emitted signals from. Because the tracking and prescription occur in real-time or quasi real-time, even if surface coil 22 is moved around during a given real-time scanning session, the position of acquisition slice 32 will be appropriately updated to provide the desired slice location relative to the new position of surface coil 22.

In one embodiment, the tracking system included in system 10 is an optical tracking system. An example of such an optical tracking system is a Passive Polaris Optical Tracking System manufactured by Northern Digital Inc. of Ontario, Canada. Tracking handpiece 24 includes an optically reflective material, such as reflective disks 34. Locator 26 includes a transmitter (to transmit signals to impinge on reflective disks 34) and a receiver (to receive returning (i.e., reflected) signals from reflective disks 34). Correspondingly, tracking unit 20 determines real-time six-degrees-of-freedom transformations (e.g., locations and orientations) of tracking handpiece 24 relative to a predetermined reference point. If the reference point is chosen to be independent of the patient being scanned (e.g., in absolute coordinates), then the reference point need be determined only once during a one-time calibration of the tracking system. In this case, the reference point need not be established every time a new scan or new patient is involved.

The tracking data transmitted from tracking unit 20 is employed by MR computer 14 to specify and/or update the location and/or orientation of acquisition slice 32 (via prescription of the gradient waveforms) in real-time or quasi real-time to acquire an MR image of the anatomy that surface coil 22 is actually pointing to. Preferably, MR computer 14 is configured to prescribe acquisition slice 32 approximately parallel to the major plane (i.e., a plane perpendicular to the longitudinal axis of handpiece 24) of surface coil 22 with a user-defined or system-constrained offset. The offset or offset distance (i.e., the perpendicular distance between surface coil 22 and acquisition slice 32) depends upon the size and shape of the specific surface coil, the anatomy being imaged, system 10 constraints, and/or the operator's determination. Alternatively, MR computer 14 may be configured to prescribe acquisition slice 32 as pre-specified by the operator with respect to surface coil 22 (e.g., not necessarily prescribing acquisition slice 32 approximately parallel to the major plane of surface coil 22).

Alternatively, the tracking system of system 10 may be an MR tracking system, an RF tracking system, a magnetic tracking system, an active or passive tracking system, or one of a variety of tracking systems capable of performing the functions described herein. It is also contemplated that system 10 may include, or provide as an alternative, a tracking system configured to guide the operator to properly locate and/or orientate surface coil 22 relative to the currently prescribed acquisition slice 32. System 10 may also provide the operator with the ability to start, pause, and/or resume the tracking system such that unnecessary or unwanted prescriptions of the acquisition slice, and computations associated therewith, are not performed when, for example, the operator has yet to determine the actual region of interest to be imaged.

In this manner, small field-of-view images generated using small localized receiver coils, such as surface coil 22, no longer present anatomy identification problems (i.e., the "narrow beam flashlight in a dark room" limitation) since the operator can freely move surface coil 22 on patient 28, as needed, to acquire and view MR images of the areas surrounding region of interest 30. Such ease in navigation and viewing of the surrounding areas of region of interest 30 effectively provides a panoramic or wide-angle view of region of interest 30. Hence, the operator can accurately identify the particular anatomy, or part thereof, in any given MR image as well as make a more informed identification or diagnosis of any anomalous anatomy, or part thereof, appearing in the MR images. For example, it is difficult to distinguish between vertebra comprising a patient's spine. Thus, if the ability to move, and accordingly generate properly updated images from surface coil 22, in a given scan were limited, then the operator may not be able to confidently identify which vertebra is being imaged.

The tracking system also eliminates the difficulty in positioning surface coil 22 relative to acquisition slice 32 such that the correct image location will be achieved in each MR image. Instead, the position of acquisition slice 32 automatically tracks relative to the position of surface coil 22 to generate high quality MR images throughout a given scanning session. Accordingly, the operator has the freedom to move and reposition surface coil 22 as he/she wants in each given scanning session, knowing that whatever anatomy surface coil 22 "points" to is the actual anatomy being shown in the MR images.

While the embodiments and application of the invention illustrated in the figures and described above are presently preferred, it should be understood that these embodiments are offered by way of example only. For example, it is contemplated that the invention may be applied to systems other than MR imaging systems or medical systems which can benefit from the use of synchronized position signals associated with transmitters and receivers such that high quality data acquisition is achieved in each instance. In another example, it is contemplated that the acquisition imaging plane may be prescribed and then system 10 provides directions to the operator to optimally position surface coil 22 to achieve desirable MR image location. Accordingly, the present invention is not limited to a particular embodiment, but extends for various modifications that nonetheless fall within the scope of the appended claims.

What is claimed is:

1. A magnetic resonance (MR) imaging system including a surface coil configured to generate an MR image having an appropriate image location, comprising a controller configured to automatically synchronize a position of an image acquisition plane with respect to a position of the surface coil, wherein each of the position of the image acquisition plane and the surface coil is defined by at least a location and an orientation.

2. The system of claim 1, wherein the controller is configured to prescribe an at least one gradient pulse of an MR pulse sequence associated with the image acquisition plane in response to the position of the surface coil on a subject of interest.

3. The system of claim 1, further comprising a monitoring apparatus coupled to the controller and configured to monitor the position of at least one of the image acquisition plane and the surface coil.

4. The system of claim 3, wherein the monitoring apparatus is a tracking system selected from a group including an optical tracking system, an MR tracking system, a magnetic tracking system, an RF tracking system, an active tracking system, and a passive tracking system.

5. The system of claim 3, wherein the monitoring apparatus is configured to track the surface coil in real-time and determine a tracking data associated with the position of the surface coil relative to a reference point.

6. The system of claim 5, wherein the controller is configured to perform the automatic synchronization in real-time based on the tracking data received from the monitoring apparatus.

7. The system of claim 3, wherein the surface coil is configured to be repositioned on a subject of interest a plurality of times during a scanning session, as desired by an operator of the MR imaging system.

8. The system of claim 7, wherein the controller is configured to perform the automatic synchronization in response to each repositioning of the surface coil.

9. The system of claim 7, wherein the MR imaging system is an open MR imaging system configured to permit the operator to reposition the surface coil relative to the subject of interest during the scanning session without repositioning the subject of interest relative to at least one magnet included in the MR imaging system.

10. The system of claim 1, wherein the surface coil is a localized radio frequency (RF) receiver coil.

11. The system of claim 1, wherein the surface coil is approximately 2–15 centimeters in dimension.

12. The system of claim 1, wherein the controller is configured to prescribe the image acquisition plane approximately parallel to the position of the surface coil with an offset.

13. The system of claim 12, wherein the offset is a distance measured approximately perpendicular between the surface coil and the image acquisition plane, and the offset is configured by at least one of a user-defined offset, a system-constrained offset, and the subject of interest.

14. A system for generating a magnetic resonance (MR) image having an appropriate image location in an MR imaging system including a surface coil, comprising:

means for monitoring a position of at least one of an image acquisition plane and the surface coil; and means for coordinating the position of the image acquisition plane with respect to the position of the surface coil, wherein each of the position of the image acquisition plane and the surface coil is defined by at least a location and an orientation.

15. The system of claim 14, wherein at least one of the means for monitoring and coordinating is performed in real-time.

16. The system of claim 14, further comprising means for positioning the surface coil on a region of interest, and wherein the means for coordinating includes means for prescribing an at least one gradient pulse of an MR pulse sequence to cause the image acquisition plane and the positioned surface coil to be located at approximately the same location on the region of interest.

17. The system of claim 14, wherein the means for monitoring includes real-time tracking of the position of the surface coil.

18. The system of claim 14, wherein the means for monitoring includes determining a tracking data associated with the position of the surface coil.

19. The system of claim 18, wherein the tracking data is utilized in the means for coordinating to configure a new position of the image acquisition plane.

20. The system of claim 18, wherein the means for coordinating includes means for prescribing at least one gradient pulse associated with the image acquisition plane.

21. The system of claim 20, wherein the means for coordinating includes means for prescribing the image acquisition plane approximately parallel to the surface coil.

22. The system of claim 14, further comprising means for moving the surface coil one or more times during a scanning session, as desired, and wherein the means for coordinating is evoked a corresponding number of times, to automatically synchronize the position of the image acquisition plane relative to the repositioned surface coil.

* * * * *

UNITED STATES PATENT AND TRADEMARK OFFICE
CERTIFICATE OF CORRECTION

PATENT NO. : 6,668,184 B1
DATED : December 23, 2003
INVENTOR(S) : Kleiman

It is certified that error appears in the above-identified patent and that said Letters Patent is hereby corrected as shown below:

Title page,
Item [*] Notice, delete the phrase "by 135 days" and insert -- by 255 days --

Signed and Sealed this

Twelfth Day of October, 2004

JON W. DUDAS
*Director of the United States Patent and Trademark Office*